United States Patent [19]

Schomberg

[11] 4,409,838

[45] Oct. 18, 1983

[54] ULTRASONIC DIAGNOSTIC DEVICE

[75] Inventor: Hermann Schomberg, Hamburg, Fed. Rep. of Germany

[73] Assignee: U.S. Philips Corporation, New York, N.Y.

[21] Appl. No.: 271,463

[22] Filed: Jun. 8, 1981

[30] Foreign Application Priority Data

Jul. 2, 1980 [DE] Fed. Rep. of Germany ....... 3024995

[51] Int. Cl.³ .......................................... G01N 29/00
[52] U.S. Cl. ..................................... 73/602; 128/660
[58] Field of Search ................. 73/602, 626, 628, 641, 73/597, 599, 606, 607; 128/660

[56] References Cited

U.S. PATENT DOCUMENTS 3,881,466  5/1975  Wilcox ................................ 73/626
4,063,549  12/1977  Beretsky et al. ..................... 73/602
4,279,157  7/1981  Schomberg et al. ................. 73/626
4,325,257  4/1982  Kino et al. ........................... 73/626

OTHER PUBLICATIONS

G. Glover et al., "Reconstruction of Ultrasound Propagation Speed Distributions in Soft Tissue: Time of Flight Tomography," IEEE Transactions on Sonics and Ultrasonics, vol. SU-24, No. 4, pp. 229-234, Jul. 1977.

Primary Examiner—Stephen A. Kreitman
Attorney, Agent, or Firm—Jack E. Haken

[57] ABSTRACT

A device and method for the determination of the internal structure of a body by means of ultrasonic waves which penetrate the body. The invention enables quantitative determination to be made of the relative acoustic parameters (absorption coefficient, body density) as a function of the location.

16 Claims, 9 Drawing Figures

ULTRASONIC DIAGNOSTIC DEVICE

FIELD OF THE INVENTION

The invention relates to a device and method for determining the internal structure of a body by means of ultrasonic waves which penetrate the body, comprising
an acoustic transducer device which is arranged to emit and to receive acoustic waves and to form measurement signals from the acoustic waves received,
a control circuit whereby the emission of a pulse-shaped acoustic wave can be performed in at least one measurement cycle consisting of emission and reception,
an electronic device for determining the internal body structure from the measurement signals, and
a unit for the display of the body structure thereby determined.

BACKGROUND OF THE INVENTION

A device of this kind is already known from U.S. Pat. No. 3,881,466. This device comprises a row of acoustic transducers whereby acoustic waves can be generated and received. Using a control circuit, each time different groups of neighbouring acoustic transducers are successively briefly pulsed in order to produce an acoustic beam, the acoustic echo pulses each time arriving being measured, thus scanning the body. In an electronic unit these acoustic echo pulses can be used to reconstruct an image of a cross-section of the body in that, for example, the measured acoustic echo pulses are reproduced as a brightness distribution in a plane after an analog treatment depending on the location of the relevant receiver and in accordance with their delay time, the brightness being dependent on the amplitude of the acoustic echo pulses. Devices of this kind are customarily referred to as B-scan devices. However, they offer only approximately true information as regards the position of acoustic interfaces in the body part exposed to the acoustic waves, because only those interfaces are recorded which reflect towards the transmitter, or which are situated at least approximately perpendicularly to the emission direction. Furthermore, it is not possible to determine the magnitude and the sign of an impedance gradient at an interface. The determination of the position of an interface is also inaccurate, because the reconstruction is based on a constant velocity of the sound and this is only approximately true. The inaccuracy is further increased in that first of all parallel acoustic waves are also liable to cross one another, so that "left" and "right" are interchanged. Moreover, multiple echos are also processed, so that in certain circumstances images of non-existent interfaces are actually formed.

INCORPORATION BY REFERENCE

The following references are incorporated herein, by reference, as background material:
R1. U.S. Pat. No. 3,881,466.
R2. P. N. T. Wells, *Biomedial Ultrasonics*, Academic Press, London, New York, San Francisco, 1977.
R3. J. F. Havlice, J. C. Taenzer, *Medical Ultrasonic Imaging: An Overview of Principles and Instrumentation*, Proc. IEEE, Vol. 67, 620-641 (1979).
R4. R. D. Melen, A. Macovski, J. D. Meindl, *Application of Integrated Electronics to Ultrasonic Medical Instruments*, Proc. IEEE, Vol. 67, 1274-1285 (1979).
R5. L. R. Rabmir, B. Gold, *Theory and Application of Digital Signal Processing*, Prentice-Hall, Englewood Cliffs, N.J., 1975.
R6. J. D. Plummer, J. D. Meindl, *A Monolithic 200—V CMOS Analog Switch*, IEEE J. Solid State Circuits, Vol. SC-11, 809-817 (1976).
R7. H. Schomberg, *A Peripheral Array Computer and its Applications. In: Parallel Computers—Parallel Mathematics* (M. Feilmeier, ed.) North-Holland Publishing Company, Amsterdam, 1977.
R8. P. Faurre, M. Depeyrot, *Elements of Systems Theory*, North-Holland Publishing Company, Amsterdam, 1977.
R9. R. J. Hanson, J. L. Phillips, *Numerical Solution of Two-Dimensional Integral Equations Using Linear Elements*, SIAM J. Numer. Anal., Vol. 15, 113-121 (1978).
R10. A. V. Oppenheim, R. W. Schaefer, *Digital Signal Processing*, Prentice-Hall, Englewood Cliffs, N.J., 1975.

SUMMARY OF THE INVENTION

The invention has for its object to provide an ultrasonic diagnostic device whereby improved and quantitative information concerning the internal structure of a body can be obtained.

This object is achieved in accordance with the invention in that
the acoustic transducer device is constructed and can be activated so that for each measurement cycle an at least approximately flat acoustic wave can be emitted thereby,
an electronic switching unit is provided for generating pulse-shaped acoustic waves having a frequency spectrum with an as large a bandwidth as possible,
in the measurement signal path between the acoustic transducer device and the electronic device there are provided respective sampling circuits which sample each corresponding measurement signal at very short time intervals in order to determine the instantaneous values thereof and which digitizes the instantaneous values measured,
there are provided Fourier transformation circuits which form respective Fourier transformed measurement signals from the digitized instantaneous values representing each corresponding measurement signal,
for the determination of frequency spectra there are provided multiplier elements for multiplying the relevant Fourier transformed measurement signals by the reciprocal value of a correction factor, the correction factor consisting of at least the product of the frequency spectrum of the emitted acoustic wave in the vicinity of the acoustic emission elements and the frequency-dependent transmission function of the relevant receiver elements of the acoustic transducer device,
the electric device is constructed so that thereby at least the distribution of the refractive index and/or the extinction coefficient within the body can be obtained from the frequency spectra.

The ultrasonic diagnostic device is constructed preferably so that in the electronic device the frequency spectra can be processed in accordance with the integral equation $$\psi_s(\vec{r}, \omega) = \int_D G(\vec{r} - \vec{r}', \omega) V(\vec{r}', \omega) \psi(\vec{r}', \omega) d^3\vec{r}', \quad (1)$$

which describes the propagation of the acoustic waves scattered by the potential $V(\vec{r}, \omega)$, with $$\nabla^2 \psi_s(\vec{r}, \omega) + \frac{\omega^2}{C_o^2} \psi_s(\vec{r}, \omega) = V(\vec{r}, \omega) \psi(\vec{r}, \omega) \quad (2)$$

$$V(\vec{r}, \omega) = \omega^2 \cdot f(\vec{r}) + g(\vec{r}) \quad (3)$$

and $$G(\vec{r} - \vec{r}', \omega) = \frac{1}{4\pi} \frac{e^{-i\frac{\omega}{C_o}|\vec{r}-\vec{r}'|}}{|\vec{r} - \vec{r}'|} \quad (3a)$$

in order to determine the functions $f(\vec{r})$ and $g(\vec{r})$ which describe the internal structure of the body, $G(\vec{r}-\vec{r}', \omega)$ being Green's function for the differential operator $$\nabla^2 + \frac{\omega^2}{C_o^2}, \psi(\vec{r}, \omega)$$

being the sum of the frequency spectra $(\psi_I(\vec{r},\omega)+\psi_s(\vec{r},\omega))$ of emitted and scattered acoustic wave, $\vec{r}$ and $\vec{r}'$ being location vectors, $\omega$ being the frequency, $C_o$ being the velocity of the acoustic waves in water, D being the scanned part of the body, and $$\psi_I(\vec{r}, \omega) = e^{i\frac{\omega}{c} x},$$

whilst $$f(\vec{r}) = \frac{1}{C_o^2} (1 - \tilde{n}(\vec{r})^2) \quad (4)$$

and $$g(\vec{r}) = \frac{1}{2}\left(\frac{1}{\rho(\vec{r})}\right) \cdot \nabla\rho(\vec{r}))^2 - \frac{1}{2\rho(\vec{r})} \nabla^2\rho(\vec{r}), \quad (5)$$

where $$\tilde{n}(\vec{r}) = n(\vec{r})(1 + ik(\vec{r})) \quad (6)$$

is the complex refractive index with its real part $n(\vec{r})$, $k(\vec{r})$ being the extinction coefficient, and $\rho(\vec{r})$ being the density of the body.

A device of this kind enables a comparatively accurate reconstruction of the internal structure of the body because inter alia quantitative results concerning the real part $n(\vec{r})$ and the imaginary part $n(\vec{r}) \cdot k(\vec{r})$ of the complex refractive index $\tilde{n}(\vec{r})$ are obtained in the scanned part of the body. Errors based on multiple echos or crossing of acoustic waves can be avoided to a great extent, because the integral equation (1) underlying the reconstruction completely describes the acoustic propagation.

The device can be advantageously used for the examination of bodies in which no excessively large impedance gradients are present. The device is particularly suitable for mammography for the detection and diagnosis of mammary cancer, for the examination of the abdomen and in many cases also for the testing of materials.

THE DRAWINGS

The drawings show embodiments in accordance with the invention. Therein:

FIG. 1 illustrates the propagation of acoustic waves in a body under examination, FIG. 2 shows a pulse/time diagram which illustrates a measurement cycle, FIG. 3 is a block and signal diagram which illustrates the processing of a measurement signal along a measurement signal path, FIG. 4 is a block diagram of an ultrasonic diagnostic device including a row of acoustic transducer elements, FIGS. 5a–e show different embodiments of acoustic transducer devices for the ultrasonic diagnostic device.

DESCRIPTION OF A PREFERRED EMBODIMENT

Figure 1:
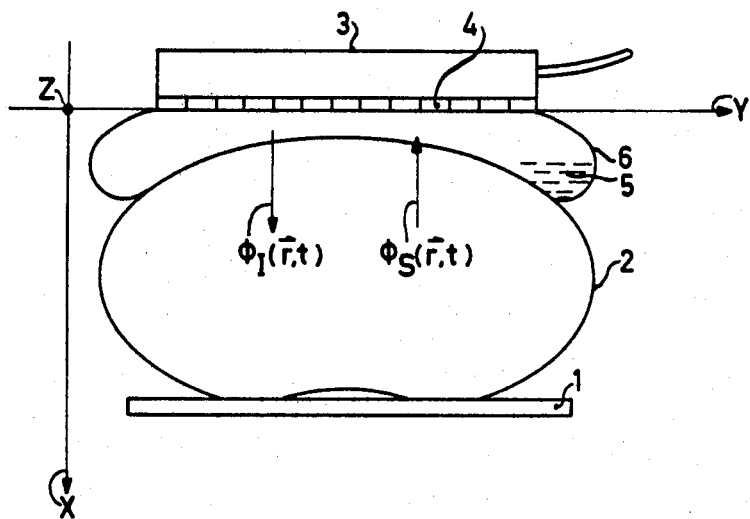

FIG. 1 is a cross-sectional view of a body 2 which is positioned on an examination table 1 and on which there is arranged an acoustic transducer device 3, the acoustic transducer elements 4 of which are arranged as a two-dimensional matrix and are capable of emitting and of receiving acoustic waves. The acoustic transducer elements, therefore, operate both as acoustic emission elements and as acoustic reception elements. The acoustic transducer device 3 is acoustically coupled to the body 2 via an acoustic coupling medium 5, for example water, which is present within a space which is bounded by an elastic foil 6 connected to the acoustic transducer device 3 in a liquidtight manner. The Y, Z plane of a three-dimensional cartesian coordinate system XYZ is situated in the plane of the transducer elements 4, the Y-axis extending along the direction of the matrix rows and the X-axis extending perpendicularly to the matrix plane in the direction of the body 2.

The principal considerations underlying the construction of the ultrasonic diagnostic device in accordance with the invention will be described hereinafter with reference to FIGS. 1 and 2. The fact that the acoustic transducer device in this case has a two-dimensional construction for the emission and reception of acoustic waves along the same direction is not be understood as a restriction in this respect. The acoustic transducer device may alternatively be constructed in another suitable manner, for example, in rows or so that it is suitable for the emission and the reception of acoustic waves extending each time in different directions, this will be described in more detail hereinafter.

The determination of the internal structure of the body 2 by means of the ultrasonic diagnostic device is realized in that the acoustic transducer device 3 emits a substantially planar acoustic wave $\phi_I(\vec{r}, t)$ into the body 2 in that, for example by simultaneously activating all the acoustic transducer elements 4. The emitted acoustic wave $\phi_I(\vec{r}, t)$ should be pulse-shaped, if possible, so as to impact a frequency spectrum of maximum bandwidth. For example, the emitted acoustic wave $\phi_I(\vec{r}, t)$ should closely approximate to a delta function for a fixed $\vec{r}$ as a function of t.

This is necessary to enable frequency $\omega$ to be used as an independent variable for the determination of, for example, the three-dimensional internal structure of a body by means of a two-dimensional acoustic transducer device. For example, the central frequency could be between 0.5 and 1.5 mHz.

Figure 2:
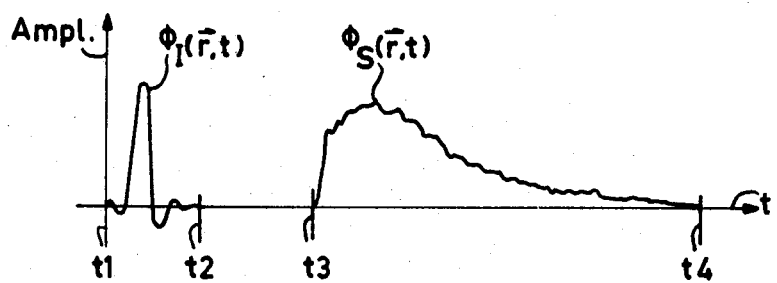

FIG. 2 shows such an acoustic wave $\phi_I(\vec{r}, t)$ emitted into the body 2 for a fixed $\vec{r}$ as a function of the time t between the instants t1 and t2. The emitted acoustic wave can be written as $$\phi_I(\vec{r}, t) = \int_{\infty}^{\infty} A(\omega) e^{i(\frac{\omega}{C_0} x - \omega t)} d\omega \quad (7)$$

in which $A(\omega)$ is the frequency-dependent amplitude or the frequency spectrum of the emitted acoustic wave $\phi_I(\vec{r}, t)$ in the vicinity of the acoustic transducer elements 4 (x=0), $\omega$ the frequency of the individual wave components, t is time, x is the distance of a location along the coordinate axis x, and Co is the velocity of the acoustic waves, for example, in water at room temperature. The function $A(\omega)$ is known or can be determined by measurement of $\phi_I(\vec{r}, t)$ and Fourier transformation. This function takes into account the pure transmission properties of the individual acoustic transducer elements 4 during the emission of the acoustic waves as well as the shape of the electrical input signals activating the acoustic transducer elements 4. After the fading of the emitted acoustic wave $\phi_I(\vec{r}, t)$, for example, all acoustic transducer elements 4 can be switched over to reception at the instant $t_3 \geq t_2$ in order to measure the acoustic wave $\phi_S(\vec{r}, t)$ which has been scattered by the body structures and which is also shown in FIG. 2, that is to say for x=0, i.e. in the transducer plane. The acoustic wave $\phi_S(\vec{r}, t)$ is defined by the formula $$\phi(\vec{r}, t) = \phi_I(\vec{r}, t) + \phi_s(\vec{r}, t) \quad (8)$$

in which $\phi(\vec{r}, t)$ is the total acoustic wave passing through the body 2; this wave represents the physically observable wave. On the basis of the difference in the time of the acoustic wave production and its measurement, therefore, the observable $\phi(\vec{r}, t)$ equals $\phi_I(\vec{r}, t)$ until the instant t2, $\phi_I(r, t)$ being defined by the formula (7). The scattered acoustic wave $\phi_S(\vec{r}, t) = \phi(\vec{r}, t) - \phi_I(\vec{r}, t)$ defined by the formula (8), however, corresponds to that observable during the measurement phase $t \geq t_3$ (see FIG. 2) in which $\phi_I(\vec{r}, t)$ has disappeared, so that $\phi_S(\vec{r}, t)$ is then measured. A measurement cycle which consists of the emission of the pulse-shaped acoustic wave $\phi_I(\vec{r}, t)$ and the reception of the scattered acoustic wave $\phi_S(\vec{r}, t)$ is terminated at the instant t4 after the fading of the scattered acoustic wave $\phi_S(\vec{r}, t)$. If the path of the acoustic waves between the acoustic transducer device 3 and the body 4 is only very short, for example, when use is made of a contact gel instead of the water reservoir, the scattered acoustic wave $\phi_S(\vec{r}, t)$ is liable to reach the acoustic transducer device 3 even before termination of the acoustic emission. In that case, the parts of the body 2 which are situated nearest to the acoustic transducer device 3 cannot be reconstructed.

The scattered acoustic wave can be written as $$\phi_S(\vec{r}, t) = \int_{-\infty}^{\infty} A(\omega) \psi_S(\vec{r}, \omega) e^{-i\omega t} d\omega \quad (9)$$

in which $\psi_S(r, \omega)$ represents the frequency spectrum of the scattered acoustic wave. $\psi_S(r, \omega)e^{-i\omega t}$ is the wave which would have been scattered if $\psi_I(r, \omega)e^{-i\omega t} = e^{i(\omega/C_0 x - \omega t)}$ had been emitted. The electrical measurement signal produced at each instant by means of the acoustic transducer elements 4 can then be written as $$\tilde{\phi}_S(\vec{r}_{ij}, t) = \int_{-\infty}^{\infty} A(\omega) B(\omega) \psi_S(\vec{r}_{ij}, \omega) e^{-i\omega t} d\omega \quad (10)$$

in which $B(\omega)$ denotes a frequency dependent transmission function and describes the reception properties of the acoustic transducer elements. $B(\omega)$ is known or can also be determined by suitable measurement (see Reference R8, page 181 et seq).

The indices i and j indicate the acoustic transducer element 4 having the coordinates $\vec{r}_{ij} = (O, Y_i, Z_j)$ which produces the measurement signal $\tilde{\phi}_S(\vec{r}_{ij}, t)$.

The determination of the frequency spectrum $\psi_S(\vec{r}_{ij}, \omega)$ from the measurement signal $\tilde{\phi}_S(\vec{r}_{ij}, t)$ (formula (10)) requires a Fourier transformation measurement signal $\tilde{\phi}_S(\vec{r}_{ij}, t)$ as well as a division of the Fourier-transformed measurement signal $\tilde{\psi}_S(\vec{r}_{ij}, \omega)$ by the variables $A(\omega)$ and $B(\omega)$, so that the frequency spectrum is $$\psi_S(\vec{r}_{ij}, \omega_1) = \frac{\tilde{\psi}_S(\vec{r}_{ij}, \omega_1)}{A(\omega_1) B(\omega_1)} \quad (11)$$

in the formula (11), the index 1 indicates the different frequencies $\omega_1$ associated with the frequency spectrum. The division indicated in the formula (11) is preferably executed so that the frequency spectrum $\tilde{\psi}_S(\vec{r}_{ij}, \omega_1)$ is multiplied by the reciprocal value of a correction factor $C_{ijl}$ which represents, for example, the product $A(\omega_1) \cdot B(\omega_1)$. This is advantageous, because the reciprocal value of the correction factor can be determined once, for all and a multiplication can be executed faster than 3 division. However, the correction factor $C_{ijl}$ can also be chosen in another suitable manner, for example as $C_{ijl} = A(\omega_1) B(\omega_1) + \epsilon_1$ (Wiener filter) for optimum treatment of noise problems. If the individual acoustic transducer elements 4 at the locations $(\vec{r}_{ij})$ were to have different emission and reception properties, $C_{ijl}$ is generally chosen as $C_{ijl} = A_{ij}(\omega_1) B_{ij}(\omega_1) + \epsilon_{ijl}$ (12) if the same transducer elements are used for the emission and reception of acoustic waves.

Figure 3:
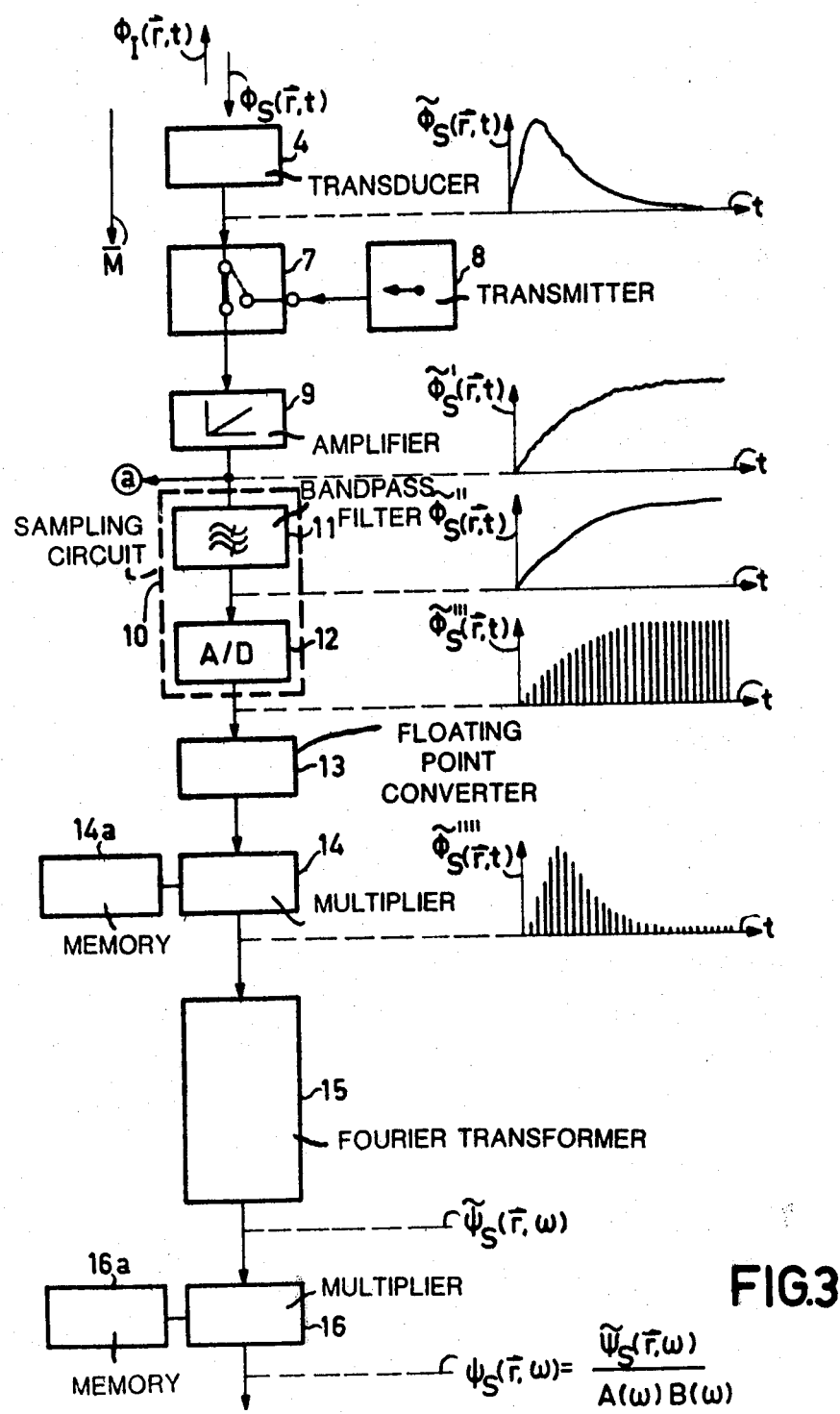

For the sake of clarity, indexing (i, j, l) is omitted hereinafter. The determination of the frequency spectrum $\psi_S(\vec{r}, \omega)$ from the measurement signal $\tilde{\phi}_S(\vec{r}, t)$ is shown in FIG. 3, and will be explained in more detail at a later stage.

If the frequency spectrum $\psi_S(\vec{r}, \omega)$ at the locations $r_{ij}$ is known for the different frequencies $\omega_1$, the internal body structure can be determined therefrom.

The object is to solve the integral equation (1) for the potential $V(\vec{r}, \omega)$, that is to say to find the functions f and g (equations (4) and (5)) so that the equation (3) solves the integral equation (1). For example, when the function f has been determined, inter alia the real refractive index $n(\vec{r})$ and the extinction coefficient $k(r)$ can be determined therefrom by means of the equations (4) and (6).

The solution of the integral equation (1) for $\psi_S$ at the location x=0, thus abbreviated:

$$\psi_S|_{x=0} = \int_D G V(\psi_I + \psi_S) d^3 \vec{r}, \quad (13)$$

can be performed by iteration. First of all, it is assumed that $\psi_S$ is very small in comparison with $\psi_I$ (Born approximation). Equation (13) then becomes $$\psi_S|_{x=0} = \int_D G V\psi_I d^3\vec{r}, \quad (14)$$

in which $$\psi_I = e^{i\omega/C_0 x} \quad (14')$$

Such an equation (14) can be solved numerically by discretization and the known $\psi_S|_{x=0}$ ($\Delta\psi_S(\vec{r}, \omega)$) (see Reference R9.)

If $\psi_S$ is not very small with respect to $\psi_I$, the solution of equation (14) can be iteratively improved, for example, by means of the "Born series". For example, if $$V^{(1)} = \omega^2 f^{(1)} + g^{(1)} \quad (15)$$

is the result of equation (14), the function $$\psi_S^{(1)} = \int_D V^{(1)}\psi^{(1)} d^3\vec{r}, \quad (16)$$

where $$\psi^{(1)} = \psi_I + \psi_S^{(0)} \quad (17)$$

and $$\psi_S^{(0)} = 0, \quad (18)$$

can be calculated everywhere, and subsequently $$\psi_S|_{x=0} = \int_D G V(\psi_I + \psi_S^{(1)}) d^3\vec{r}, \quad (19)$$

can similarly be solved with respect to V and the result can be called $V^{(2)}$, and so on. Equation (19) is then solved in a similar manner to equation (16). After i steps, the iteration method is interrupted. From the result $$V^{(i)} = \omega^2 f^{(i)} + g^{(i)} \quad (20)$$

$n(\vec{r})$ and $k(\vec{r})$ can then be determined and reproduced, for example, on a monitor, printer or the like.

For the determination of the frequency spectra $\psi_S(\vec{r}, \omega)$ from the electrical measurement signals $\phi_S(\vec{r}, t)$, the ultrasonic diagnostic device in accordance with the invention comprises measurement signal paths $\overline{M}$ shown in FIG. 3 (the indexing (i, j) of the location vectors $\vec{r}$ has been omitted for the sake of simplicity). If the determination of the internal structure of the body 2 has to be executed by means of a single measurement cycle, each of the acoustic transducer elements 4 must be connected to a corresponding measurement signal path $\overline{M}$ of its own. However, it is also possible to execute a so-called scanning mode in which several measurement cycles are carried out and in which on each successive occasion a different group of acoustic transducer elements 4 is switched over to reception after the emission of a planar acoustic wave $\phi_I(\vec{r}, t)$. This is advantageous, because the number of measurement signal paths $\overline{M}$ can be reduced and hence also the costs of the circuitry of such an ultrasonic diagnostic device.

A measurement signal path $\overline{M}$, in which the measurement signal $\phi_S(\vec{r}, t)$ can be processed in real time, comprises, for example, an acoustic transducer element 4 by means of which acoustic waves can be emitted as well as received ($\phi_I(\vec{r}, t)$ and $\phi_S(\vec{r}, t)$ respectively), said element 4 having suitable transmission properties for the transmission of pulse-shaped acoustic waves with a wideband frequency spectrum. The acoustic transducer element 4 is connected to a switch 7 which isolates the element from the measurement signal path $\overline{M}$ during the emission of acoustic waves and electrically connects the element to a transmitter 8 which supplies the necessary electrical signals for the pulsed activation of the acoustic transducer element 4. For the further processing of the electrical measurement signal $\tilde{\phi}_S(\vec{r}, t)$ which is supplied by the acoustic transducer element 4 and which corresponds to the received acoustic wave $\phi_S(\vec{r}, t)$, however, the acoustic transducer element 4 is connected, via the switch 7, to an amplifier 9 which amplifies the measurement signals $\tilde{\phi}_S(\vec{r}, t)$ in proportional to the delay time of the acoustic waves in the body 2, so that measurement signals $\tilde{\phi}_S(\vec{r}, t)$ are obtained with at least approximately the same signal intensity (see Reference R2, chapter 6).

These signals $\tilde{\phi}_S^1(\vec{r}, t)$ can be derived from an output a in order to be applied to a known B-scan processing circuit (see Reference R2, R3 and R4) which will be described in detail with reference to FIG. 4. The ultrasonic diagnostic device in accordance with the invention, therefore, may comprise, for example, a B-scan diagnostic device or may act as an addition thereto.

The output of the amplifier 9 is connected to a sampling circuit 10 which comprises a bandpass filter 11 for limiting the bandwidth of the measurement signal $\tilde{\phi}_S^1(\vec{r}, t)$ to approximately half the sampling frequency of the subsequent analog-to-digital converter 12 which is also associated with the sampling circuit 10. This is necessary in order to satisfy the Nyquist condition (for example, see Reference R8, page 148 et seq).

The analog-to-digital converter 12 samples the measurement signal $\tilde{\phi}_S^{11}(\vec{r}, t)$ whose bandwidth has been limited in order to determine its instantaneous values, for example, at a sampling frequency of from 2 to 5 MHz and presents the sampled instantaneous values in digital form ($\tilde{\phi}_S^{111}(\vec{r}, t)$). For a sampling frequency of 2 MHz, a sampling interval of 500 ns occurs. The resolution of the analog-to-digital converter 12 amounts to 12 bits or more, and the previously executed amplification (amplifier 9) of the measurement signal ensures that all instantaneous values can be sampled with substantially the same relative accuracy.

To the output of the analog-to-digital converter 12 or the sampling circuit 10 there is connected a converter 13 which converts the format of the digitized measurement signal $\tilde{\phi}_S^{111}(\vec{r}, t)$ from the fixed-point representation in which it leaves the analog-to-digital converter 12, into the floating-point representation; this can again take place within 500 ns for each sampling point. It is thus achieved that after a multiplier element 14 which follows the converter 13 and in which the measurement signal $\tilde{\phi}_S^{111}(\vec{r}, t)$ is multiplied by the reciprocal value of the gain factor of the amplifier 9, all instantaneous values of the measurement signal $\tilde{\phi}^{111}(r, t)$ thus obtained can be represented in digital form with the same relative accuracy. The reciprocal values of the gain factors may be stored, for example, in a memory 14a which is connected to the multiplier element 14.

The output of the multiplier element 14 is connected to a Fourier transformation circuit 15. Using this circuit, a Fourier transformed measurement signal $\tilde{\psi}_S(r, \omega)$ is obtained from the measurement signal $\tilde{\phi}_S^{1111}(\vec{r}, t)$. Subsequently, in a multiplier element 16 which is connected to the Fourier transformation circuit 15, the Fourier transformed measurement signal $\psi_S(\vec{r}, \omega)$ is multiplied by the reciprocal value of the correction factor $A(\omega) \cdot B(\omega)$ in order to obtain a frequency spectrum $\psi_S(r, \omega)$. The reciprocal value of the correction factor is stored, for example, in the memory 16a which is connected to the multiplier element 16.

The frequency spectrum $\psi_S(r, \omega)$ is then processed in the electronic device 21 (FIG. 4) in order to determine the internal body structure.

The Fourier transformation itself can also be executed in real time. For an assumed penetration depth of the acoustic waves in the body 2 of 20 cm, an acoustic velocity of 1500 m/s and a sampling interval of 500 ns, the signal length of the measurement signal is chosen to be, for example, 512 sampling points. The use of so-called "pipeline FFT" processors, described in detail in Reference R5, chapter 10, is a condition for such processing of the measurement signals. For a length of the measurement signal of 512 sampling points, $\log_2 512 = 9$ "butterfly processors" (see Reference R5, chapter 10) must then be successively connected for each pipeline FFT processor. Their clock period should correspond to the clock period of the elements 12, 13, etc. When two measurement signals are combined in order to form a "complex signal", half the number of pipeline FFT processors can be omitted (see Reference R10, chapter 3), so that only one Fourier transformation circuit 15 is required for each pair of measurement signal paths $\overline{M}$.

Figure 4:
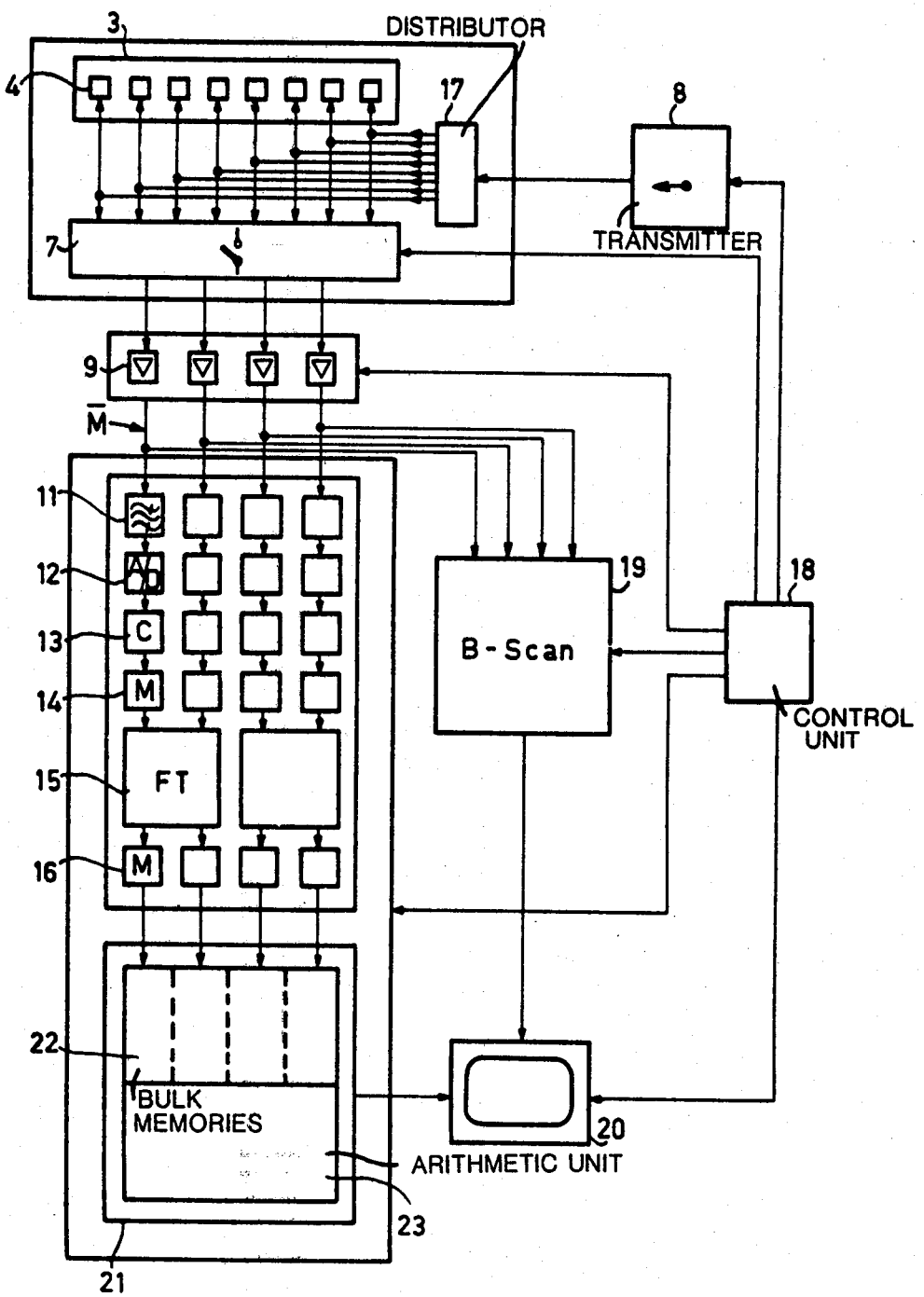

FIG. 4 shows a block diagram of the complete ultrasonic diagnostic device. The elements which correspond to the FIGS. 1 and 3 are denoted by corresponding reference numerals. The reference numeral 3 again denotes the acoustic transducer device, but only one row of acoustic transducer elements 4 thereof is shown. The electrical signals generated by the transmitter 8 can be distributed by means of a distributer 17 so that all transducer elements 4 simultaneously emit acoustic waves. Using the switch 7, the acoustic transducer elements 4 can be selected whose measurement signals have to be distributed over the measurement signal paths $\overline{M}$, present. The switch 7 or the distributer 17 may be formed, for example, as integrated modules (see Reference R6).

FIG. 4 shows, by way of example, four measurement signal paths M and eight acoustic transducer elements 4, so that these elements have to be activated at least twice for the emission of acoustic waves. In practice, the acoustic transducer device 3 may comprise a substantially larger number of transducer elements 4 in each row, for example, 128. The number of rows may also be very large, for example, 16, 32, or 64. The number of measurement signal paths $\overline{M}$ present then determines how often all the acoustic transducer elements 4 have to be simultaneously activated.

Figure 5A:
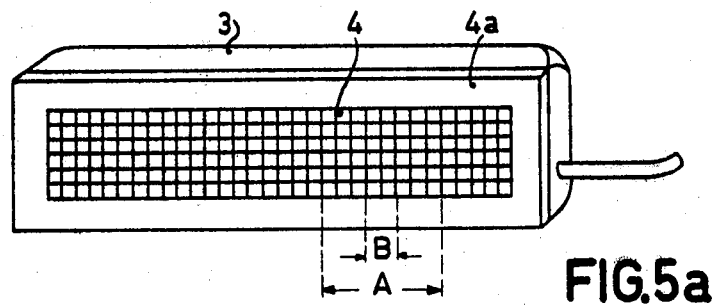

Obviously, it is alternatively possible to activate, preceding in the row direction, each time different, associated groups A (see FIG. 5a) of column-wise arranged acoustic transducer elements 4 for the emission of planar waves. The switch 7, which is controlled by the control unit 18, as are the transmitter 8 and the distributor 17, is then actuated so that between successive activations of the acoustic transducer elements 4, different transducer elements 4 (group B) which are situated within a group A, are on each occasion co-lumn-wise connected to the measurement signal paths $\overline{M}$. However, if the number of measurement signal paths $\overline{M}$ should correspond to the total number of transducer elements 4, a single emission of an acoustic wave would suffice, and the switch 7 can be dispensed with.

As has already been stated, the measurement signals $\phi_S^1(\vec{r}, t)$ present at the output of the amplifier 9 can be used for a conventional B-scan. To achieve this, the outputs of the amplifier 9 are connected to a B-scan processing circuit 19 which can be controlled by means of the control unit 18 and which is connected to a monitor 20 for the display of the B-scan.

Furthermore, the outputs of the multiplier elements 16 are connected to an electronic unit 21 which determines, by means of the frequency spectra $\psi_S(\vec{r}, \omega)$, the internal structure of the body 2 which can also be displayed on the monitor 20. The electronic unit 21 comprises bulk memories 22 for the storage of the data produced by each measurement signal path $\overline{M}$ and also an arithmetic unit 23 for calculating the body structure from said data. The elements 11 to 16 are also controlled by means of the unit 18. The arithmetic unit 23 may be, for example, a conventional minicomputer or microcomputer, but may be further extended supplemented by a parallel field calculator, for example, as described in Reference R7.

The FIGS. 5a–e show various embodiments of acoustic transducer devices for the ultrasonic diagnostic device in accordance with the invention. The acoustic transducer device 3 shown in FIG. 5a comprises acoustic transducer elements 4 which are arranged in the form of a matrix in one plane. These elements are suitable for the emission as well as the reception of acoustic waves. The acoustic transducer elements 4 have transmission properties with a comparatively large bandwidth for the processing of pulse-shaped signals. They are surrounded by a so-called guard transducer 4a which is also situated in the matrix plane and which is activated simultaneously with the acoustic transducer elements 4 for the emission of acoustic waves. The guard transducer 4a ensures that the acoustic wave field generated by the acoustic transducer elements 4 is rendered particularly flat. The front of the acoustic transducer device 3 is covered with an elastic foil 6 as shown in FIG. 1, an acoustic coupling medium 5, for example, water being present between said foil and the acoustic transducer device 3. Obviously, the body 2 to be examined can alternatively be acoustically coupled to the acoustic transducer device 3 via a contact gel, so that no foil is required.

Figure 5B:
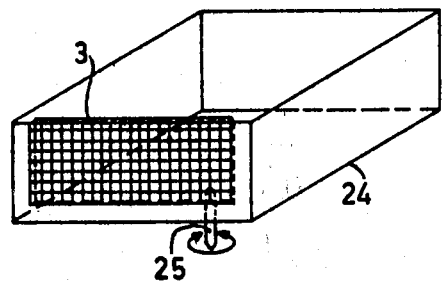

As is shown in FIG. 5b, the transducer device 3 may alternatively be arranged in a tank 24 which is to be filled with an acoustic coupling medium and may form, for example, a wall for the bottom of the tank 24 (the guard transducer 4a has been omitted for the sake of clarity). The tank 24 consists, for example, of a rectangular tub-like container, one side or the bottom of which is formed by the acoustic transducer device 3, whilst the body to be examined can be introduced from the top via an opening. The tank 24 may be journalled on a shaft 25 so as to be rotatable or pivotable about the body.

Figure 5C:
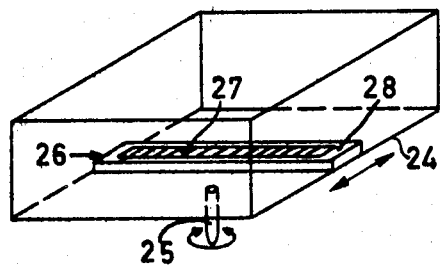

Obviously, an acoustic transducer device may alternatively consist of only a single row 26 of acoustic transducer elements 27 which is surrounded by a guard transducer 28 (FIG. 5c). The row 26 is then arranged on the bottom of the tank 24 and is displaceable perpendicularly to the direction of the row. A row of this kind may also be arranged on a sidewall of the tank 24 in a similar manner, for example, the direction of the row extending perpendicularly to that of a notional extension of the rotary shaft.

The tank 24 may also accommodate several acoustic transducer devices which are arranged about a notional extension of the shaft 25. For example, FIG. 5d shows four acoustic transducer devices 3a-d which constitute the four sidewalls of the tank 24. The acoustic transducer elements 4 of a acoustic transducer device 3a may then be simultaneously activated to emit a planar acoustic wave, whilst subsequently the acoustic transducer elements 4 of all acoustic transducer devices 3a-d are switched over to reception for the determination of measurement signals. Similarly, four matrix rows 26 which are situated in a plane perpendicularly to the rotary shaft 25 can also be activated.

In a further embodiment of the device shown in FIG. 5d, the bottom 29 of the tank 24 is also fully covered by an acoustic transducer device as shown in FIG. 5b for the emission of planar acoustic waves. During an examination of a body 2, only the acoustic transducer device arranged on the bottom 29 is activated, whilst after the emission of the pulse-shaped planar acoustic wave, all the acoustic transducer devices in the tank 24 are switched over to reception. The acoustic transducer device for emitting planar sound waves which is arranged on the bottom 29, however, can in this case alternatively consist of a single, plate-shaped acoustic transmitter which completely covers the bottom. For the reception of the acoustic waves, only the acoustic transducer elements arranged on the sidewalls of the tank could then be switched on.

Figure 5E:
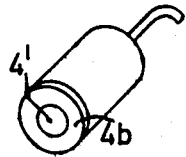
Figure 5D:
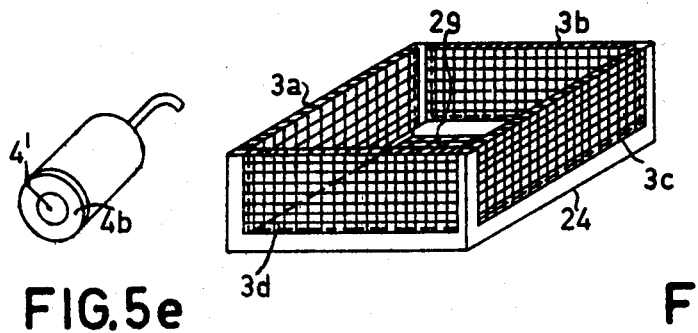

Obviously, an acoustic transducer device may also consist of a single acoustic transducer element 4' as shown in FIG. 5e which is larger than the acoustic transducer elements 4, 27 and which is possibly surrounded by a guard transducer 4b. An acoustic transducer element 4' of this kind could be mounted to be displaceable with respect to the body 2 by means of a mechanical guide, for example, within the tank 24, the relevant positions of the acoustic transducer element 4' with respect to each other also being determined by means of said guide device. For example, an element of this kind could be used instead of a matrix-row device for scanning one line-path across a body. For a reproduction of the distribution of structures within the body to be determined, however, the individual positions of the transducer element along the row are necessary; these positions are then provided by the guide device.

I claim:

1. A device for determining the internal structure of a body by means of ultrasonic waves which penetrate the body comprising:
   acoustic transducer means for periodically emitting pulses of planar acoustic waves having a large-bandwidth frequency spectrum into the body, for receiving echos of the waves which are scattered in the body and for forming measurement signals which represent the emitted and received waves;
   one or more signal processing paths which include:
   i. means for calculating the Fourier transform of the measurement signals and
   ii. means for calculating the frequency spectra of the waves by multiplying the Fourier transform of the measurement signal by correction factors which comprise the product of the frequency spectrum of the emitted acoustic waves in the vicinity of the transducer means and a frequency dependent transmission function of the transducer means;
   means which directly calculate the distribution of the refractive index within the body from the frequency spectra; and
   means for displaying the calculated distribution.

2. A device for determining the internal structure of a body by means of ultrasonic waves which penetrate the body comprising:
   acoustic transducer means for periodically emitting pulses of planar acoustic waves having a large-bandwidth frequency spectrum into the body, for receiving echos of the waves which are scattered in the body and for forming measurement signals which represent the emitted and received waves;
   one or more signal processing paths which include:
   i. means for calculating the Fourier transform of the measurement signals; and
   ii. means for calculating the frequency spectra of the waves by multiplying the Fourier transform of the measurement signal by correction factors which comprise the product of the frequency spectrum of the emitted acoustic waves in the vicinity of the transducer means and a frequency dependent transmission function of the transducer means;
   means which directly calculate the distribution of the extinction coefficient within the body from the frequency spectra; and
   means for displaying the calculated distribution.

3. A device as claimed in claim 1 or 2 wherein the means which calculate the distribution function to solve the integral equation $$\psi_S(\vec{r},\omega) = \int_D G(\vec{r} - \vec{r}',\omega) V(\vec{r}',\omega)\psi(\vec{r}',\omega) d^3\vec{r}',$$

which describes the propagation of the acoustic waves scattered by the potential $V(\vec{r},\omega)$, with $$\Delta^2 \psi_S(\vec{r},\omega) + \frac{\omega^2}{C_0^2} \psi_S(\vec{r},\omega) = V(\vec{r},\omega)\psi(\vec{r},\omega),$$

$$V(\vec{r},\omega) = \omega^2 \cdot f(\vec{r}) + g(\vec{r})$$

and $$G(\vec{r} - \vec{r}',\omega) = -\frac{1}{4\pi} \frac{e^{-i\frac{\omega}{C_0}|\vec{r} - \vec{r}'|}}{|\vec{r} - \vec{r}'|}$$

in order to determine the functions $f(\vec{r})$ and $g(\vec{r})$, which describes the internal structure of the body, $G(\vec{r}-\vec{r}', \omega)$ being Green's function for the differential operator $\nabla^2+(\omega^2/C_0^2)$, $\psi(\vec{r}, \omega)$ being the sum of the frequency spectra $(\psi_I(\vec{r}, \omega)+\psi_S(\vec{r},\omega))$ of the emitted and scattered acoustic waves, r and r' being location vectors, $\omega$ being the frequency, Co being the velocity of acoustic waves in water, D being the scanned part of the body and $$\psi_I(\vec{r},\omega) = \frac{\omega}{e^{iC}} \alpha,$$

while $$f(\vec{r}) = \frac{1}{C_0^2}(1 - \tilde{n}(\vec{r})^2)$$

and $$g(\vec{r}) = \frac{1}{2}\left(\frac{1}{\rho(\vec{r})} \cdot \nabla\rho(\vec{r})\right)^2 - \frac{1}{2\rho(\vec{r})} \nabla^2\rho(\vec{r}),$$

where $n(r) = n(r)(1 + i\, k(r))$ is the complex refractive index with its real part n(r), k(r) being the extinction coefficient, and ρ(r) being the density of the body.

4. A device as claimed in claim 3 wherein the transducer means function to emit pulses of ultrasonic waves having a pulse shape which approximates a delta function.

5. A device as claimed in claim 1 or 2 wherein the acoustic transducer means comprise a plurality of acoustic transducer elements for the emission and reception of acoustic waves, said elements being arranged in a row.

6. A device as claimed in claim 5 wherein the transducer means comprise transducer elements arranged in a two-dimensional matrix.

7. A device as claimed in claim 1 or 2 wherein the transducer means comprise a plurality of separate transducer elements and further comprising a plurality of separate signal processing paths, each signal processing path being connected to independently process the measurement signals from a distinct group of one or more transducer elements.

8. The apparatus of claim 7 comprising separate means for calculating the Fourier transform for each signal processing path.

9. A device for determining the distribution of the complex ultrasonic refractive index within a body comprising:
pulse-echo measuring means for emitting pulses of planar waves of ultrasound energy into the body and for producing signals which represent the echos of the energy which are scattered from internal body structures;
Fourier transformer means for extracting the frequency spectra of the emitted and received ultrasound waves from the signals; and
means for directly calculating the spatial distribution of the complex refractive index in the body from the extracted frequency spectra.

10. The apparatus of claim 9 further comprising means for generating and displaying a B-scan of the internal structures of the body and means for displaying the distribution of the complex refractive index in conjunction with the display of the B-scan.

11. The apparatus of claims 9 or 10 wherein the means for calculating the distribution of the complex refractive index comprise means which calculate the distribution function to solve the integral equation $$\psi_S(\vec{r},\omega) = \int_D G(\vec{r} - \vec{r}',\omega) V(\vec{r}',\omega)\psi(\vec{r}',\omega) d^3\vec{r}',$$

which describes the propagation of the acoustic waves scattered by the potential V ($\vec{r}'$,ω), with $$\Delta^2 \psi_S(\vec{r},\omega) + \frac{\omega^2}{C_o^2} \psi_S(\vec{r},\omega) = V(\vec{r},\omega)\psi(\vec{r},\omega),$$

$$V(\vec{r},\omega) = \omega^2 \cdot f(\vec{r}) + g(\vec{r})$$
and $$G(\vec{r} - \vec{r}',\omega) = -\frac{1}{4\pi} \frac{e^{-i\frac{\omega}{C_o}|\vec{r} - \vec{r}'|}}{|\vec{r} - \vec{r}'|}$$

in order to determine the functions f($\vec{r}$) and g($\vec{r}$), which describes the internal structure of the body,
G($\vec{r}-\vec{r}'$,ω) being Green's function for the differential operator $\nabla^2 + \omega^2/C_o^2$, $\psi(\vec{r},\omega)$ being the sum of the frequency spectra ($\omega_i(\vec{r},\omega) + \omega_S(\vec{r},\omega)$) of the emitted and scattered acoustic waves, r and r' being location vectors, ω being the frequency, Co being the velocity of acoustic waves in water, D being the scanned part of the body and $$\psi_i(\vec{r},\omega) = \frac{\omega}{e^{iC}} \alpha,$$

while $$f(\vec{r}) = \frac{1}{C_o^2}(1 - \tilde{n}(\vec{r})^2)$$

and $$g(\vec{r}) = \frac{1}{2}\left(\frac{1}{\rho(\vec{r})} \cdot \nabla\rho(\vec{r})\right)^2 - \frac{1}{2\rho(\vec{r})} \nabla^2\rho(\vec{r}),$$

where
$\tilde{n}(\vec{r}) = n(\vec{r})(1 + i\, k(\vec{r}))$ is the complex refractive index with its real part n($\vec{r}$), k($\vec{r}$) being the extinction coefficient, and ρ($\vec{r}$) being the density of the body.

12. A method for determining the internal structure of a body comprising:
transmitting pulses of planar waves of wideband ultrasonic energy into the body;
detecting echos of said pulses which are scattered from internal structures of the body and producing electrical signals representative thereof;
calculating the frequency spectra of the transmitted and received ultrasound energy; and
directly calculating the distribution of the complex ultrasonic refractive index within the body from said frequency spectra.

13. The method of claim 12 further comprising displaying the distribution of the complex refractive index as a representation of the internal body structures.

14. The method of claim 12 or 13 wherein the calculation of the complex refractive index comprises solution of the integral equation $$\psi_S(\vec{r},\omega) = \int_D G(\vec{r} - \vec{r}',\omega) V(\vec{r}',\omega)\psi(\vec{r}',\omega) d^3\vec{r}',$$

which describes the propagation of the acoustic waves scattered by the potential V ($\vec{r}'$,ω), with $$\Delta^2 \psi_S(\vec{r},\omega) + \frac{\omega^2}{C_o^2} \psi_S(\vec{r},\omega) = V(\vec{r},\omega)\psi(\vec{r},\omega),$$

$$V(\vec{r},\omega) = \omega^2 \cdot f(\vec{r}) + g(\vec{r})$$
and

-continued $$G(\vec{r} - \vec{r}',\omega) = -\frac{1}{4\pi} \frac{e^{-i\frac{\omega}{Co}|\vec{r} - \vec{r}'|}}{|\vec{r} - \vec{r}'|}$$

in order to determine the functions $f(\vec{r})$ and $g(\vec{r})$, which describes the internal structure of the body, $G(\vec{r}-\vec{r}',\omega)$ being Green's function for the differential operator $\nabla^2 + \omega^2/Co^2$, $\psi(\vec{r},\omega)$ being the sum of the frequency spectra ($\psi_I(\vec{r},\omega) + \psi_S(\vec{r},\omega)$) of the emitted and scattered acoustic waves, r and r' being location vectors, $\omega$ being the frequency, Co being the velocity of acoustic waves in water, D being the scanned part of the body and $$\psi_I(\vec{r},\omega) = \frac{\omega}{e^i C} a,$$

while $$f(\vec{r}) = \frac{1}{Co^2}(1 - \tilde{n}(\vec{r})^2)$$

and $$g(\vec{r}) = \frac{3}{4}\left(\frac{1}{\rho(\vec{r})} \cdot \nabla \rho(\vec{r})\right)^2 - \frac{1}{2\rho(\vec{r})} \nabla^2 \rho(\vec{r}),$$

where $$\tilde{n}(\vec{r}) = n(\vec{r})(1 + i\, k(\vec{r}))$$

is the complex refractive index with its real part $n(\vec{r})$, $k(\vec{r})$ being the extinction coefficient, and $\rho(\vec{r})$ being the density of the body.

15. A method of calculating the distribution of the complex ultrasonic refractive index in a body from data which represents the frequency spectra of pulses of wideband ultrasonic energy which are introduced into the body as planar waves and of echos of said pulses which are scattered from the body comprising:
solving the integral equation $$\psi_S(\vec{r},\omega) = \int_D G(\vec{r} - \vec{r}',\omega)\, V(\vec{r}',\omega)\psi(\vec{r}',\omega)d^3\vec{r}',$$

which describes the propagation of the acoustic waves scattered by the potential $V(\vec{r},\omega)$, with $$\Delta^2 \psi_S(\vec{r},\omega) + \frac{\omega^2}{Co^2}\psi_S(\vec{r},\omega) = V(\vec{r},\omega)\psi(\vec{r},\omega),$$

$$V(\vec{r},\omega) = \omega^2 \cdot f(\vec{r}) + g(\vec{r})$$

and $$G(\vec{r} - \vec{r}',\omega) = -\frac{1}{4\pi} \frac{e^{-i\frac{\omega}{Co}|\vec{r} - \vec{r}'|}}{|\vec{r} - \vec{r}'|}$$

in order to determine the functions $f(\vec{r})$ and $g(\vec{r})$, which describes the internal structure of the body, $G(\vec{r}-\vec{r}',\omega)$ being Green's function for the differential operator $\nabla^2 + \omega^2/Co^2$, $\psi(\vec{r},\omega)$ being the sum of the frequency spectra ($\psi_I(\vec{r},\omega) + \psi_S(\vec{r},\omega)$) of the emitted and scattered acoustic waves, r and r' being location vectors, $\omega$ being the frequency, Co being the velocity of acoustic waves in water, D being the scanned part of the body and $$\psi_I(\vec{r},\omega) = \frac{\omega}{e^i C} a,$$

while $$f(\vec{r}) = \frac{1}{Co^2}(1 - \tilde{n}(\vec{r})^2)$$

and $$g(\vec{r}) = \frac{3}{4}\left(\frac{1}{\rho(\vec{r})} \cdot \nabla \rho(\vec{r})\right)^2 - \frac{1}{2\rho(\vec{r})} \nabla^2 \rho(\vec{r}),$$

where
$$\tilde{n}(\vec{r}) = n(\vec{r})(1 + i\, k(\vec{r}))$$
is the complex refractive index with its real part $n(\vec{r})$, $k(\vec{r})$ being the extinction coefficient, and $\rho(\vec{r})$ being the density of the body.

16. The method of ultrasonic diagnosis comprising displaying the distribution of the complex refractive index obtained in accordance with the method of claim 15 as an image which represents internal structures of the body.

* * * * *

UNITED STATES PATENT AND TRADEMARK OFFICE
CERTIFICATE OF CORRECTION

PATENT NO. : 4,409,838
DATED : October 18, 1983
INVENTOR(S) : HERMANN SCHOMBERG

It is certified that error appears in the above—identified patent and that said Letters Patent is hereby corrected as shown below:

In the claims:

Column 13, Claim 3

"$n(r) = n(r) (1 + i\ k(r))$" should read

--$\tilde{n}(\vec{r}) = n(\vec{r}) (1 + i\ k(\vec{r}))$--.

Signed and Sealed this

Tenth Day of January 1984

[SEAL]

Attest:

GERALD J. MOSSINGHOFF

*Attesting Officer*  *Commissioner of Patents and Trademarks*